United States Patent [19]

Gorham

[11] Patent Number: 5,242,240

[45] Date of Patent: Sep. 7, 1993

[54] CLAMPING DEVICE FOR A SURGICAL RETRACTOR

[75] Inventor: Adelbert Gorham, Burnsville, Minn.

[73] Assignee: Minnesota Scientific, Inc., St. Paul, Minn.

[21] Appl. No.: 778,512

[22] Filed: Oct. 17, 1991

[51] Int. Cl.$^5$ ............................................. A61B 17/00
[52] U.S. Cl. ................................... 403/391; 403/389; 128/20
[58] Field of Search ................ 128/20; 403/389, 391

[56] References Cited

U.S. PATENT DOCUMENTS

| | | |
|---|---|---|
| 4,617,916 | 10/1986 | LeVahn et al. ............ 128/20 |
| 4,718,151 | 1/1988 | LeVahn et al. ............ 128/20 X |
| 4,949,707 | 8/1990 | LeVahn et al. ............ 128/20 |
| 5,020,195 | 6/1991 | LeVahn ............ 128/20 X |
| 5,025,780 | 6/1991 | Farley ............ 128/20 |

FOREIGN PATENT DOCUMENTS 1042699 11/1958 Fed. Rep. of Germany ...... 403/391

Primary Examiner—Randolph A. Reese
Assistant Examiner—Anthony Knight

[57] ABSTRACT

A clamping device having a number of components includes a retaining mechanism that retains the components in an assembled state for cleaning and sterilization. The device includes a bolt and a nut that bring first and second clamping leg portions toward each other to a clamping position. The nut is held is rotatable relationship with the first clamping leg by a retaining ring. Similarly, the bolt is held in rotatable engagement with the second leg portion by a second retaining ring.

4 Claims, 2 Drawing Sheets

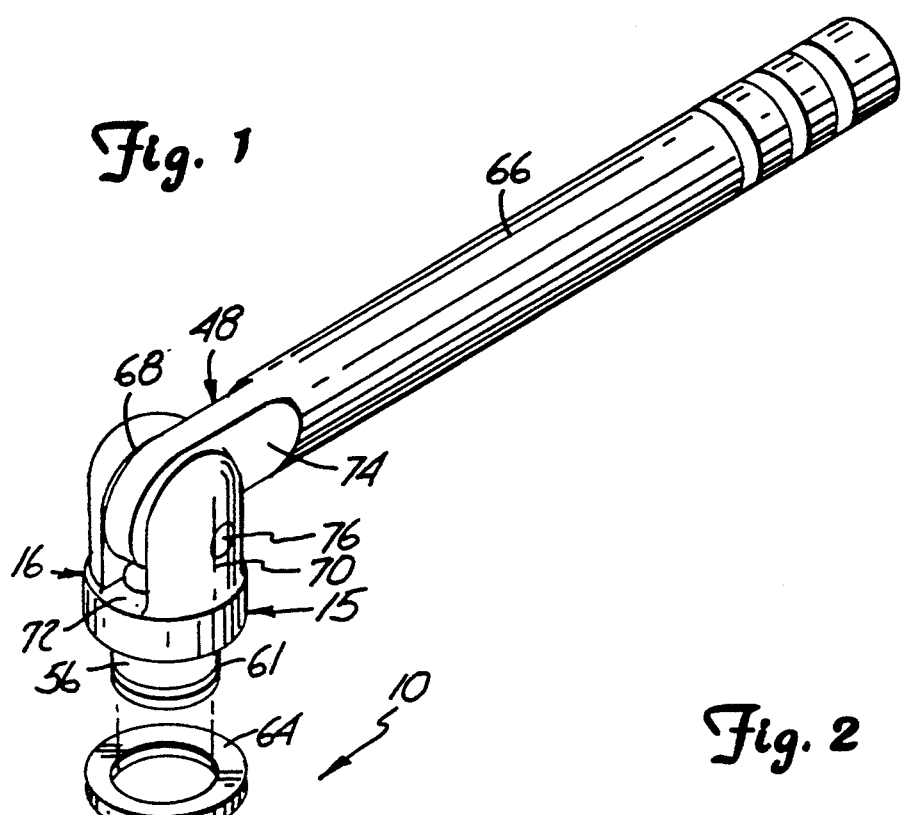
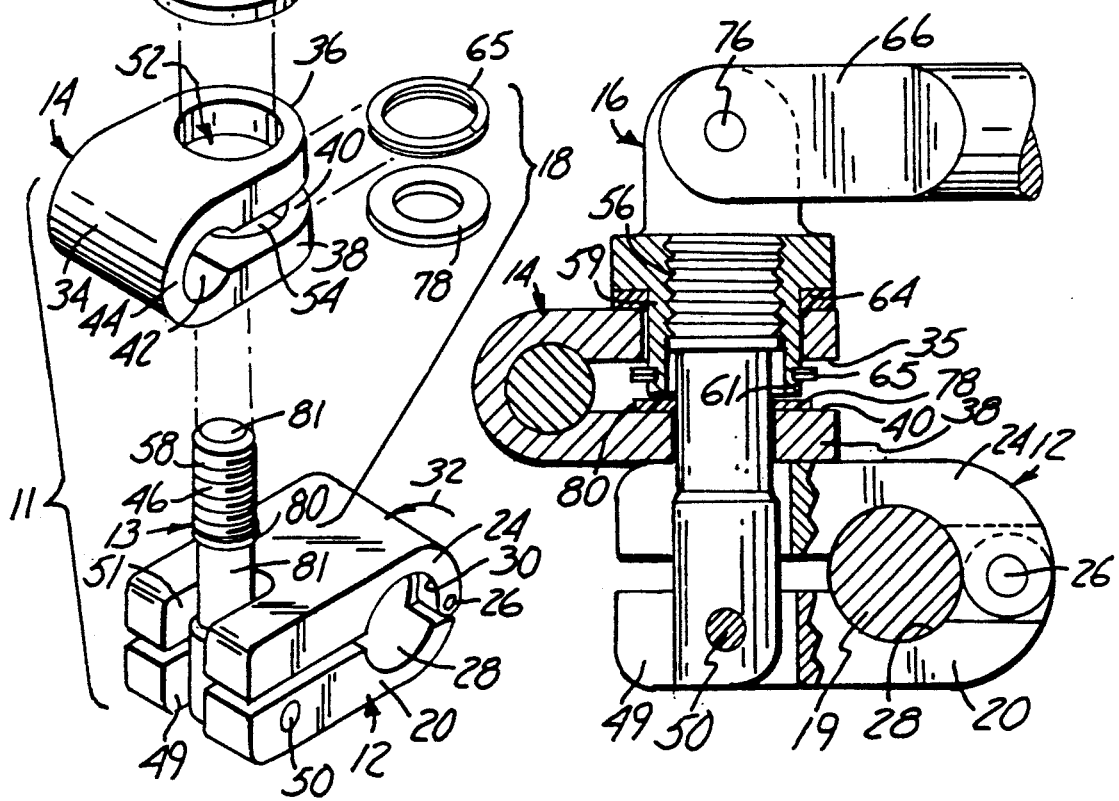

CLAMPING DEVICE FOR A SURGICAL RETRACTOR

BACKGROUND OF THE INVENTION

The present invention relates to surgical retractor support devices. In particular, it relates to a clamping mechanism for a surgical retractor.

In abdominal and chest surgery, it is customary to use a retractor that is mounted to a retractor support that extends over an operating table. The retractor is used to hold back tissue proximate the surgical incision enabling the surgeon to work in areas such as the abdominal area or chest cavity.

Retractors include a blade and a handle that is typically a shaft to which the blade is attached. The retractor is attached to the retractor support by some type of clamping mechanism that engages the handle of the retractor.

Clamping mechanisms include a number of components. It has been the practice of hospital personnel to disassemble the clamping mechanisms for cleaning and sterilization. Problems occur when components are lost or misplaced, and when knowledge of how the clamping device is reassembled is forgotten.

The Farley U.S. Pat. No. 5,025,780 is retained in an assembled state when in a non-clamping position. The device includes a clamping mechanism having a first clamping leg portion and a second clamping leg portion that are movable toward and away from each other. Each clamping leg portion has an aperture, the apertures being coaxially disposed with respect to each other. The device further includes a bolt that extends through the first aperture and a nut that extends through the second aperture, the nut and the bolt being threadably engagable with each other to provide a force for bringing the first and second clamping leg portions to a clamping position. A retaining mechanism for retaining the bolt, nut, and the clamping mechanism in an assembled state includes a first retaining ring engaging the nut, the first retaining ring having a diameter greater than the diameter of the first aperture and being disposed on the side of the upper leg portion that faces the lower leg portion. The retaining mechanism further includes a second retaining ring engaging the bolt, the second retaining ring having a diameter greater than the diameter of the second aperture and disposed on a side of the lower leg portion facing the upper leg portion.

SUMMARY OF THE INVENTION

The present invention includes a clamping device for use in a surgical retractor support. The clamping device generally includes a clamping means. The clamping means includes a clamping portion having a first clamping means for clamping a first rod of a surgical retractor support and a second clamping means for clamping a second rod of surgical retractor support. The clamping device also includes a means for providing a single force to bring the first and second clamping means to a clamping position. The means includes a bolt portion having an annular lip that extends through the clamping portions. The means further includes a locking nut portion for engaging the bolt portion such that the first and second clamping means are placed in a clamping position. The clamping device additionally includes a retaining means for maintaining assembly of the bolt portion, clamping means and locking nut portion when the locking nut portion and bolt portion are disengaged. The retaining means includes a captivating ring engaged with the annular lip of the bolt portion positioned proximately to the clamping portion.

BRIEF DESCRIPTION OF THE DRAWINGS

FIG. 1 is an exploded perspective view of one embodiment of the clamping device of the present invention.

FIG. 2 is a cross-sectional view of the clamping device of FIG. 1.

DETAILED DESCRIPTION OF THE PREFERRED EMBODIMENTS

Figure 3:
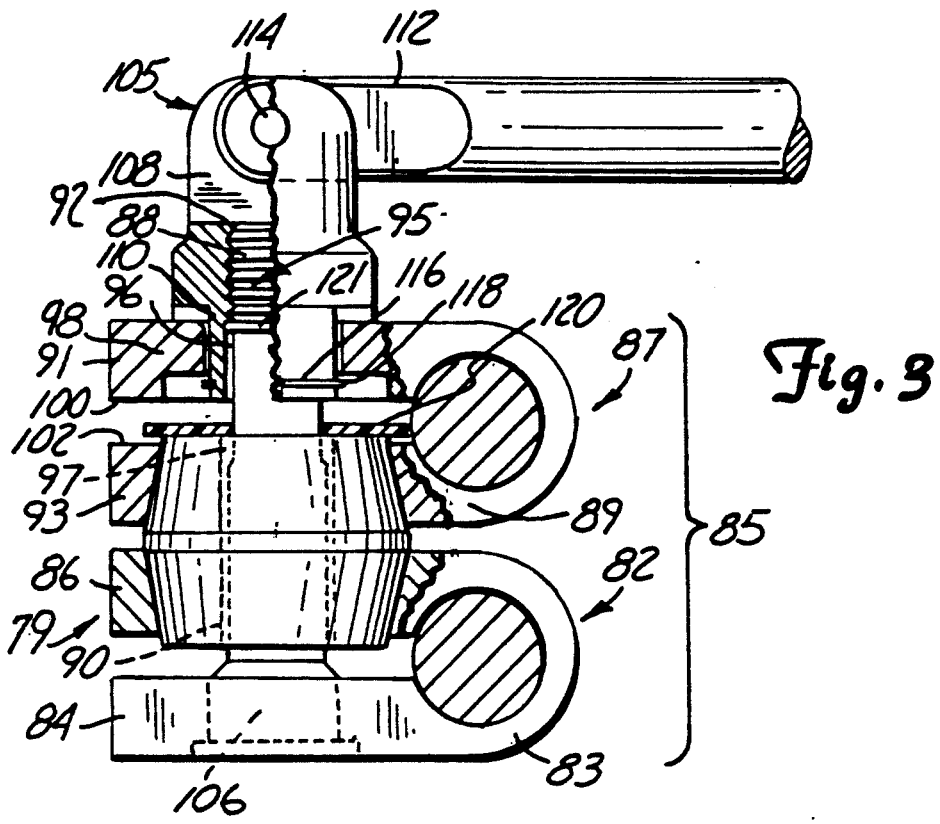
FIG. 3 is a cross-sectional view of an alternative embodiment of the clamping device of the present invention.

The clamping device of the present invention is generally illustrated at 10 in FIGS. 1 and 2. The clamping device includes a bolt 13, a clamping mechanism 11, a bolt engaging handle section 15, and a clamp retaining mechanism 18. The retaining mechanism 18 retains the clamping device in an assembled state for cleaning and sterilization. However, the various components can be placed in a disengaging position so that thorough cleaning and sterilization of the device is carried out. Retaining the device in an assembled state for cleaning and sterilization eliminates parts being lost, and avoids errors in reassembly.

The clamping mechanism 11 includes a first clamping section 12 and a second clamping section 14. The first clamping section 12 includes a first clamping portion 20 and a second clamping portion 24 pivotally attached to the first clamping section 20 by a pivot pin 26. The first clamping portion 20 includes a first clamping groove 28, and the second clamping portion 24 includes a second clamping groove 30. It will be appreciated that when the second clamping portion 24 is pivoted about the pivot pin 26 in the direction indicated by arrow 32, that the clamping portions 20 and 24 are placed in clamping engagement such that the clamping grooves 28 and 30 define the clamping bore in which a retractor rod section 19 is disposed as illustrated in FIG. 2.

The second clamping section 14 preferably includes a unitary main body 34 having an upper clamping leg 36 and a lower clamping leg 38, as best illustrated in FIGS. 1 and 2. The unitary main body 34 is preferably machined from a single block of stainless steel. The upper and lower clamping legs 36 and 38 are spaced apart from each other by a slot 40 that extends between the legs 36 and 38 from one end of the second clamping mechanism 14 to a clamping bore 42 disposed approximate an opposite end 44. The clamping bore 42 receives and clamps a rod section 22 as best illustrated in FIG. 2. The legs 36 and 38 are resiliently movable with respect to each other such that the clamping bore 42 is reduced sufficiently in size to frictionally clamp the rod section 22 when the legs 36 and 38 are moved toward each other.

The clamping mechanisms 12 and 14 are placed in clamping engagement by engagement of the bolt 13 and the bolt engaging handle section 15. The bolt 13 preferably includes a threaded bolt portion 46. The bolt portion 46 is disposed at one end in a slot 49 in the first clamping portion 20 of the first clamping section 12. A pivot pin 50 pivotally attaches the bolt 13 to the first clamping section 12. The second clamping portion 24 of the first clamping section 12 also includes a slot 51 in which the bolt 13 resides when the first clamping section 12 is in a clamping position as best illustrated in FIGS. 1 and 2.

The legs 36 and 38 of the second clamping section 14 include apertures 52 and 54, respectively, through which the threaded bolt 13 extends. It will be appreciated that the second clamping section 14 is rotatable about the axis of the threaded bolt 13 and therefore rotatable with respect to the first clamping section 12.

The bolt engaging handle section 15 includes an internally threaded nut 56. The nut 56 engages a threaded end 58 of the bolt 13, as best illustrated in FIG. 2. The threaded nut 56 has a lower necked-down section 59 that extends through the aperture 52 of the leg 36. A friction ring 64 is disposed between the clamping section 14 and the nut 56 to facilitate turning the threaded nut 56. A handle 66 is pivotally attached through the threaded nut 56 to provide a member for turning the nut 56.

The bolt engaging handle section 15 additionally has first and second upwardly extending retaining members 68 and 70 respectively, separated by a slot 72. The handle 66 of the section 15 has a slot engaging portion 74 that is disposed in the slot 72 and is pivotally attached to the threaded nut 56 by a pin 76 that extends between the first and the second retaining members 68 and 70 and through the handle 66. The handle 66 is pivotal about the pin 76 from one side of the threaded nut 56 to the other side of the nut 56, approximately 180°, to facilitate turning the nut 56.

The retaining mechanism 18 for maintaining assembly of the components of the clamping device 10 includes a captivating ring 78 that engages an annular lip 80 on the threaded bolt 13. The annular lip 80 is preferably disposed on a side of the threaded portion 46 opposite a free end 81 of the bolt 13.

The annular lip 80 has a diameter less than the diameter of the aperture 54, permitting the insertion of the bolt through the aperture 54. The captivating ring has an inner diameter that is slightly less than the outside diameter of the annular lip 80, however, the inside diameter of the captivating ring is greater than the outside diameter of the shank 81 of the bolt 13. The captivating ring is positioned below the annular lip and above an upper surface 40 of the lower clamping leg 38 by snapping the captivating ring 80 over the annular lip. The captivating ring is made of a material that is resilient enough to permit positioning of the ring past the annular lip. Since the outside diameter of the lip is greater than the inside diameter of the aperture of the captivating ring and the outside diameter of the ring 78 is greater than the diameter of the aperture 54, the combination of ring and lip prevents the bolt from being pulled back through the aperture 54 once the ring is in place below the lip 80. The above described arrangement permanently and rotatably attaches the bolt 13 to the clamping section 12, and since the bolt 13 is attached to the clamping section 14, the clamping section 14 is also permanently attached in one assembly.

The captivating ring 78 is preferably made from a flexible material that is strong, light weight, and autoclavable. In the most preferred embodiment, the captivating ring is made from Victrex PEEK, a poly(aryletherketone), a linear aromatic polymer, manufactured by ICI of Great Britain. Victrex PEEK is described in U.K. Pat. No. 432 02 24, which is herein incorporated by reference. Properties of Victrex PEEK are described in Table 1, set forth below.

It is desirable for the present invention that the captivating ring be insoluble in all common solvents and have resistance to a wide range of organic and inorganic liquids. It is also desirable that the captivating ring is made from a material that offers excellent tribological properties at temperatures of 300° F. under a wide range of conditions and retain the mechanical properties. Victrex PEEK, for instance, can be used for thousands of hours at temperatures in excess of 250° F. high pressure water environments without any significant degradation in properties. It is also important that the captivating ring be made of a material that flexes, in one embodiment, as much as ⅛ inches before it snaps the annular lip.

TABLE 1

| Property | Test Method | Units | 150G/151G | 380G/381G | 450G | 150GL20* |
|---|---|---|---|---|---|---|
| GENERAL | | | | | | |
| Form | — | — | Granules | Granules | Granules | Granules |
| Colour | — | — | Grey | Grey | Grey | Brown |
| Relative Density: | | | | | | |
| (Crystalline) | ASTM D792 | — | 1.32 | 1.32 | 1.32 | 1.43 |
| (Amorphous) | ASTM D792 | — | 1.26 | 1.26 | 1.26 | — |
| Filler content | — | % | 0 | 0 | 0 | 20 |
| Typical level of crystallinity | — | % | 35 | 35 | 35 | 35 |
| Mould shrinkage Across/With Flow | — | % | — | 1.2/0.7 | 1.2/0.7 | — |
| Water absorption: | | | | | | |
| 24 hr @ 73° F. | ASTM D570 | % | 0.5 | 0.5 | 0.5 | — |
| Equilibrium @ 73° F. | ISO R62A | % | 0.5 | 0.5 | 0.5 | — |
| MECHANICAL | | | | | | |
| Tensile strength | | | | | | |
| @ 73° F. (Break/Yield) | ASTM D638(5 mm/min) | psi | 14,500(y) | 14,500(y) | 14,500(y) | 18,850(b) ∎ |
| @ 482° F. (Break/Yield) | ASTM D638(5 mm/min) | psi | 1,740(y) | 1,740(y) | 1,740(y) | 3,480(b) ∎ |
| Elongation at break @ 73° F. | ASTM D638(5 mm/min) | % | — | — | 50 | — |
| Elongation at yield @ 73° F. | ASTM D638(5 mm/min) | % | 4.9 | 4.9 | 4.9 | — |
| Tensile modulus 1% secant @ 73° F. | ASTM D638 | psi | — | — | 522 | — |
| Flexural modulus | | | | | | |
| @ 73° F. | ASTM D790 | psi | 594,500 | 594,500 | 594,500 | 942,500 ∎ |
| @ 248° F. | ASTM D790 | psi | 580,100 | 580,100 | 580,100 | 942,500 ∎ |
| @ 482° F. | ASTM D790 | psi | 43,500 | 43,500 | 43,500 | 217,500 ∎ |

TABLE 1-continued

PHYSICAL PROPERTIES

| Property | Test Method | Units | 150G/ 151G | 380G/ 381G | 450G | 150GL20* |
|---|---|---|---|---|---|---|
| Flexural strength | | | | | | |
| @ 73° F. | ASTM D790 | psi | 24,650 | 24,650 | 24,650 | 27,850 ■ |
| @ 248° F. | ASTM D790 | psi | 14,500 | 14,500 | 14,500 | 19,580 ■ |
| @ 482° F. | ASTM D790 | psi | 1,800 | 1,800 | 1,800 | 7,690 ■ |
| Shear strength (Ultimate) | ASTM D3846 | psi | 7,690 | 7,690 | 7,690 | — |
| Shear modulus @ 73° F. | | psi | — | 188,500 | 188,500 | — |
| Compressive strength @ 73° F. (with flow) | ASTM D695 | psi | — | 17,110 | 17,110 | 23,490 ■ |
| Compressive strength @ 73° F. (across flow) | ASTM D695 | psi | — | 17,250 | 17,250 | 19,430 ■ |
| Charpy impact strength @ 73° F. | | | | | | |
| 0.08 in notch radius | BS2782 (351A) | ft lbin$^{-1}$ | — | 6.7 | 6.7 | — |
| 0.01 in notch radius | BS2782 (351A) | ft lbin$^{-1}$ | — | 0.16 | 0.16 | — |
| Izod impact strength @ 73° F. | | | | | | |
| Notched 0.01 in radius, 0.14 in depth | ASTM D256 | ft lbin$^{-1}$ | 1.12 | 1.57 | 1.57 | — |
| Unnotched | ASTM D256 | ft lbin$^{-1}$ | — | No break | No break | — |
| Poissons ratio @ 73° F.: | | | | | | |
| with flow | ASTM D638 | — | — | 0.4 | 0.4 | — |
| across flow | ASTM D638 | — | — | 0.4 | 0.4 | — |
| Rockwell hardness: | | | | | | |
| R scale | ASTM D785 | — | — | 126 | 126 | 125 ■ |
| M scale | ASTM D785 | — | — | 99 | 99 | 102 ■ |
| THERMAL | | | | | | |
| Melting Point (peak of melting endothermy) | DSC | °F. | 649 | 644 | 644 | 649 |
| Glass transition temperature, Tg (onset value) | DSC | °F. | 289 | 289 | 289 | 289 |
| Specific heat capacity | — | Btu lb$^{-1}$ °F.$^{-1}$ | — | — | 0.08 | — |
| Coefficient of thermal expansion: | | | | | | |
| <Tg | ASTM D696 | $10^{-5}$ °F.$^{-1}$ | 2.6 | 2.6 | 2.6 | — |
| >Tg | ASTM D696 | $10^{-5}$ °F.$^{-1}$ | 6.0 | 6.0 | 6.0 | — |
| Heat Distortion temperature, 264 psi | ASTM D648 | °F. | 311 | 320 | 320 | — |
| Thermal conductivity | ASTM C177 | Btu-in/hr ft$^2$ °F. | 1.75 | 1.75 | 1.75 | — |
| UL continuous use temperature (estimated) | UL746B | °F. | 482 | 482 | 482 | 482 |

(y) = Value at yield
(b) = Value at break
■ Estimated Value
*These materials are anisotropic and properties will vary with direction.

Another suitable material for use in the captivating ring component 78 of the retaining portion 18 includes the 1,000 series ULTEM manufactured by General Electric (Rochester, N.Y.). Properties of this material are described in Table 2.

TABLE 2

TYPICAL PROPERTY VALUES

| PROPERTY | ASTM TEST METHOD | UNITS | ULTEM 1000 RESIN | ULTEM 1010 RESIN |
|---|---|---|---|---|
| MECHANICAL | | | | |
| Tensile Strength, Yield | D638 | psi(MPa) | 15,200(105) | 15,200(105) |
| Tensile Modulus, 1% Secant | D638 | psi(MPa) | 430,000(3,000) | 430,000(3,000) |
| Tensile Elongation, Yield | D638 | % | 7-8 | 7-8 |
| Tensile Elongation, Ultimate | D638 | % | 60 | 60 |
| Flexural Strength | D790 | psi(MPa) | 22,000(150) | 22,000(150) |
| Flexural Modulus, Tangent | D790 | psi(MPa) | 480,000(3,300) | 480,000(3,300) |
| Compressive Strength | D695 | psi(MPa) | 21,900(150) | 21,900(150) |
| Compressive Modulus | D695 | psi(MPa) | 480,000(3,300) | 480,000(3,300) |
| Gardner Impact Strength | — | in-lb(N-m) | 320(36) | 300(34) |
| Izod Impact Strength | D256 | ft-lbs/in(J/m) | | |
| Notched, ⅛" (3.2 mm) | | | 1.0(50) | 0.6(30) |
| Unnotched, ⅛" (3.2 mm) | | | 25(1,300) | 25(1,300) |
| Shear Strength, Ultimate | — | psi(MPa) | 15,000(100) | 15,000(100) |
| Rockwell Hardness | D785 | — | M109 | M109 |
| Taber Abrasion (CS 17, 1 kg) | D1044 | mg. wt. loss/ 1000 cycles | 10 | 10 |
| THERMAL | | | | |
| Deflection Temperature, Unannealed @ 66 psi, ¼" (0.45 MPa, 6.4 mm) | D648 | °F.(°C.) | 410(210) | 405(207) |
| @ 264 psi, ¼" (1.82 MPa, 6.4 mm) | | | 392(200) | 387(197) |

TABLE 2-continued

| PROPERTY | ASTM TEST METHOD | UNITS | TYPICAL PROPERTY VALUES ULTEM 1000 RESIN | ULTEM 1010 RESIN |
|---|---|---|---|---|
| Vicat Softening Point, Method B | D1525 | °F.(°C.) | 426(219) | 426(219) |
| Thermal Index, UL Bulletin 746B | UL746B | °F.(°C.) | 338(170) | 338(170) |
| Coefficient of Thermal Expansion, 0 to 300° F. (−18 to 150° C.), Mold Direction | D696 | in/in/°F. (m/m/°C.) | $3.1 \times 10^{-5}$ $(5.6 \times 10^{-5})$ | $3.1 \times 10^{-5}$ $(5.6 \times 10^{-5})$ |
| Thermal Conductivity | C177 | Btu-in/hr-ft² °F.(W/m °C.) | 1.5(0.22) | 1.5(0.22) |

The retaining mechanism also includes the retaining ring 65. The retaining ring 65 rotatably attaches the bolt engaging handle section 15 with the first clamping section 12. The retaining ring 65 has an outside diameter that is larger than the aperture 52 of the upper leg 35, thereby preventing the necked-down portion 59 from being pulled out of the aperture 52. The nut 56 includes an annular groove 61 that is engaged by the retaining ring 65, as best illustrated in FIG. 2.

The retaining mechanism 18 permits the bolt 13 to be loosened in a manner that exposes the threaded end portion 58 for cleaning without detaching the bolt 13 or the bolt engaging handle section 15 from the clamping mechanism 11. Instead, when the bolt 13 is disengaged from the bolt engaging handle section 15, the threaded end portion of the bolt 13 is exposed with the captivating ring 78 catching the upper surface of the lower clamping leg 38 to retain attachment of the bolt 13 to the clamping section 14.

The retaining mechanism 18 can be used on any type of clamping device that includes a bolt and nut combination for providing a clamping force to a clamping mechanism. For example, an alternative embodiment of the present invention is generally indicated at 79 in FIG. 3. The device 79 includes a clamping mechanism 85 having a lower clamping section 82 and an upper clamping section 87. The lower clamping section 82 includes a unitary main body 83 having a first clamping leg 84 and a second clamping leg 86. The upper clamping section 87 likewise includes a unitary main body 89 having an upper clamping leg 91 and a lower clamping leg 93. A captivating ring 120 is disposed on an upper surface 102 of the lower clamping leg 93 of the unitary main body 89.

The clamping device 79 also includes a bolt 95 having a threaded bolt portion 88 that extends through an aperture 90 in the lower clamping section 82. The bolt 95 is secured to the lower clamping section 82 by a base portion 106. The threaded bolt portion 88 also extends through an aperture 96 of the upper clamping section 87. The threaded bolt portion includes a threaded upper end 92 and an annular lip 121 disposed below the threaded bolt portion.

The annular lip 121 is also disposed below a lower surface 100 of the upper clamping leg 91 and above an upper surface 102 of the lower clamping leg 93 of the unitary main body 89.

The clamping device 79 also includes a bolt engaging handle section 105. The bolt engaging handle section 105 is similar to the section 15 described with reference to FIG. 2 and includes an internally threaded nut portion 108. The threaded nut portion 108 engages the threaded bolt portion 88 of the bolt 95. The threaded nut portion 108 has a lower necked-down section 110 that extends through the aperture 96 of the upper clamping section 87.

To facilitate turning, and thereby provide a clamping or compressive force to the clamping sections 82 and 87, the threaded nut 108 of the bolt engaging handle section 105 includes a handle 112 pivotally attached by a pin 114 to the threaded nut 108. The handle 112 is pivoted about the pin 114 from one side of the threaded nut 108 to the other side of the threaded nut 108 to facilitate turning the bolt engaging handle section 105.

The clamping device 79 also includes a retaining mechanism that includes a retaining ring 118 engaging the threaded bolt 95 similarly as the ring 65 of FIG. 2 and the captivating ring 120 engaging an annular lip 121 similarly as the captivating ring 78 of FIG. 2. The retaining ring 118 has a diameter that is larger than the diameter of the aperture 96, thereby retaining the bolt engaging handle section 105 in rotatable attachment to the clamping section 87. Similarly, the ring 120 has a diameter that is larger than the diameter of the aperture 97 in the lower leg 93, thereby retaining the bolt 95 in rotatable attachment to the upper clamping section 87 since the annular lip 121 prevents the bolt 95 from disengaging. The ring 120 is made from a similar material as the washer 80 discussed with reference to the embodiment of FIG. 2.

Figure 4:
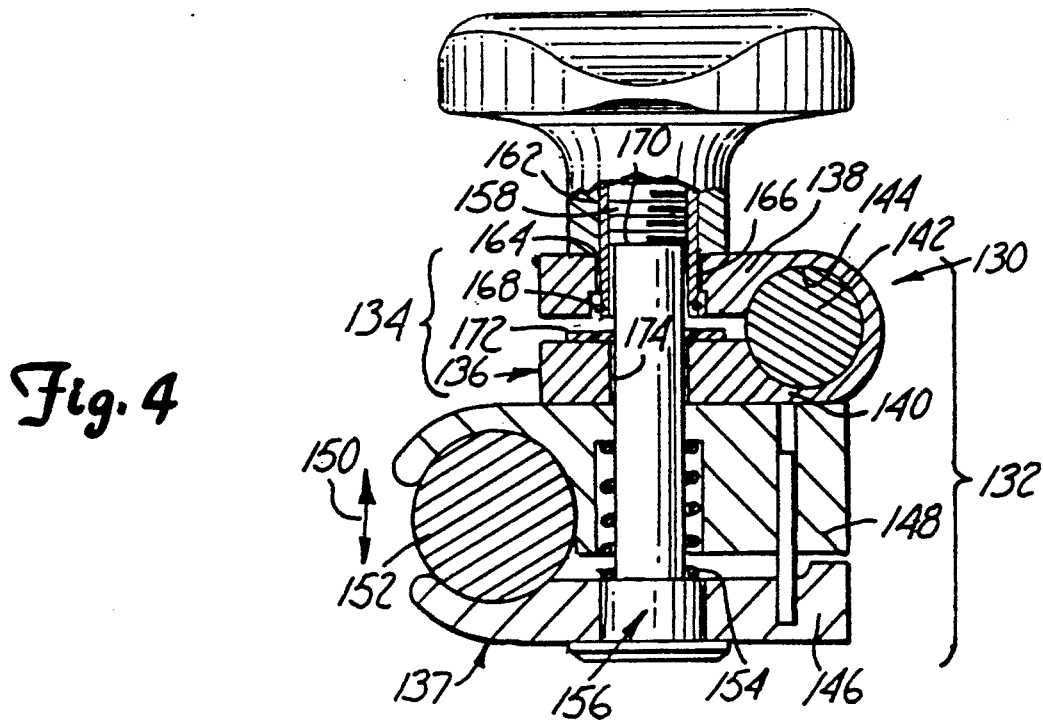
FIG. 4 is a cross-sectional view of yet another alternative embodiment of the clamping device of the present invention.

In yet another alternative embodiment of the device of the present invention generally indicated at 130 in FIG. 4, the device includes a clamping mechanism 132 that is held together by a retaining mechanism 134. Similar to the embodiments illustrated in FIGS. 2 and 3, the device 130 includes an upper clamping section 136 and a lower clamping section 137. The upper clamping section 136 is preferably made of a unitary body having an upper leg 138 and a lower leg 140 that are resiliently movable together to engage a rod 142 that is disposed within a bore 144. The lower clamping section 137 includes a lower clamping finger 146 and an upper clamping finger 148 that are movable toward and away from each other as generally indicated by arrow 150, to engage a rod 152. A coil spring 154 biases the clamping fingers 146 and 148 away from each other.

The device further includes a bolt 156 that has an upper threaded portion 158. A knob 160 having an internal threaded portion 162 is threadably engagable with the threaded portion 158 of the bolt 156 to provide a compressive force to the clamping mechanism 132, thereby placing the clamping mechanism in a clamping position.

To retain the clamping device in an assembled state, the knob 160 includes a shank portion 164 that is disposed through an aperture 166 of the upper clamping leg 138. A retaining ring 168 engages the shank portion 164, and has a diameter greater than the diameter of the aperture 166 to retain the knob 160 in rotatable engagement with the upper leg portion 138 of the upper clamping section 136.

The bolt 156 has an annular lip 170 that is disposed just below the threaded portion 158. A captivating ring 172 that is similar to the ring 120 of FIG. 3, and the ring 80 of FIG. 2, is disposed on an upper surface of the leg 140 of the upper clamping section 136 The ring 172 has an inner diameter that is less than the outer diameter of the annular lip 170, and an outer diameter that is greater than the diameter of an aperture 174 of the lower leg portion 140, thereby retaining the bolt 156 in rotatable attachment to the clamping section 136, along with the lower clamping section 137.

Although the present invention has been described with reference to preferred embodiments, workers skilled in the art will recognize that changes may be made in form and detail without departing from the spirit and scope of the invention.

What is claimed is:

1. A clamping device for use in a surgical retractor support, the device comprising:

clamping means having a first clamping leg portion and a second clamping leg portion, the clamping leg portions movable toward and away from each other between a clamping and a non-clamping position, each clamping leg portion having first and second respective coaxial apertures disposed therein;

means for bringing the first and second clamping portions to a clamping position including a nut extending through the first aperture and a bolt extending through the second aperture, the nut and bolt each having threaded portions and being threadably engagable with each other and the bolt including an annular lip positioned on a shaft of the bolt proximate the threaded portion of the bolt; and means for retaining the bolt, nut, and clamping means in an assembled state, including:

a retaining ring engaging the nut, the retaining ring having a diameter greater than a diameter of the first aperture and being disposed on a side of the first leg portion that faces the second leg portion; and a washer engaging the shaft of the bolt on a side of the annular lip opposite the threaded portion of the bolt, with the annular lip being greater in diameter than an inside diameter of the washer, with the washer having an outside diameter greater than the second aperture, and with the washer being disposed on a side of the second leg portion facing the first leg portion so as to retain the bolt within the second aperture.

2. The device of claim 1 wherein the washer is made of a polymeric material that withstands temperatures in the approximate range of 300–500° F. for 10 to 30 minutes without deformation.

3. The device of claim 1 wherein the washer is made of a poly(aryletherketone).

4. The device of claim 1 and wherein the clamping means includes a first clamping mechanism including the first and second clamping leg portions, and a second clamping mechanism attached to the bolt.

* * * * *